US009603548B2

(12) United States Patent
Ashe

(10) Patent No.: US 9,603,548 B2
(45) Date of Patent: *Mar. 28, 2017

(54) SYSTEM AND METHOD FOR MAGNETIC POSITION TRACKING

(71) Applicant: Ascension Technology Corporation, Shelburne, VT (US)

(72) Inventor: Westley S. Ashe, Hinesburg, VT (US)

(73) Assignee: Ascension Technology Corporation, Shelburne, VT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/193,344

(22) Filed: Jun. 27, 2016

(65) Prior Publication Data

US 2016/0302872 A1     Oct. 20, 2016

Related U.S. Application Data

(63) Continuation of application No. 13/534,666, filed on Jun. 27, 2012.

(51) Int. Cl.
*A61B 34/20* (2016.01)
*A61B 5/06* (2006.01)
*G01B 7/00* (2006.01)
*A61B 8/00* (2006.01)

(52) U.S. Cl.
CPC ............ *A61B 5/062* (2013.01); *A61B 8/4254* (2013.01); *A61B 34/20* (2016.02); *G01B 7/003* (2013.01); *A61B 2034/2051* (2016.02); *A61B 2090/378* (2016.02)

(58) Field of Classification Search
CPC ....... A61B 8/4254; A61B 5/062; A61B 34/20; A61B 2034/2051; A61B 2090/378; G01B 7/003; G01B 7/14; G01R 33/00
See application file for complete search history.

(56) References Cited

U.S. PATENT DOCUMENTS

| 3,717,749 A | 2/1973 | Rogers |
| 4,305,035 A | 12/1981 | Mach |
| 4,611,169 A | 9/1986 | Hermann |
| 4,945,305 A | 7/1990 | Blood |
| 5,239,474 A | 8/1993 | Eaton |
| 5,276,282 A | 1/1994 | Russell |
| 5,353,795 A | 10/1994 | Souza |
| 5,377,678 A | 1/1995 | Dumoulin et al. |
| 5,557,206 A | 9/1996 | Won |

(Continued)

*Primary Examiner* — Jermele M Hollington
*Assistant Examiner* — Suresh K Rajaputra
(74) *Attorney, Agent, or Firm* — Fish & Richardson P.C.

(57) ABSTRACT

An improved system for magnetic position tracking of a device includes a magnetic transmitter, a magnetic sensor, a computing system and a polarity inverter. The magnetic transmitter includes at least one transmitter coil that outputs a transmitted magnetic field having a time derivative component. The magnetic sensor includes at least one sensor coil that has coil terminals having a polarity, and the sensor coil is responsive to the time derivative component of the transmitted magnetic field and outputs a sensor signal. The computing system computes position and angular orientation data of a device based on the sensor signal and the polarity inverter is configured to connect to the coil terminals and to cause the polarity of the coil terminals to be reversed according to a switching signal.

28 Claims, 6 Drawing Sheets

(56) References Cited

U.S. PATENT DOCUMENTS

| | | | |
|---|---|---|---|
| 5,600,330 A | 2/1997 | Blood | |
| 5,744,953 A | 4/1998 | Hansen | |
| 5,831,260 A | 11/1998 | Hansen | |
| 5,953,683 A | 9/1999 | Hansen | |
| 6,172,499 B1 | 1/2001 | Ashe | |
| 6,246,231 B1 | 6/2001 | Ashe | |
| 6,316,934 B1 | 11/2001 | Amorai-Moriya | |
| 6,362,625 B1 | 3/2002 | Wiegert | |
| 6,385,482 B1 | 5/2002 | Boksberger et al. | |
| 6,487,516 B1 | 11/2002 | Amorai-Moriya | |
| 6,528,991 B2 | 3/2003 | Ashe | |
| 6,754,596 B2 | 6/2004 | Ashe | |
| 6,754,609 B2 | 6/2004 | Lescourret | |
| 6,781,380 B1 | 8/2004 | Wiegert | |
| 6,784,660 B2 | 8/2004 | Ashe | |
| 6,856,823 B2 | 2/2005 | Ashe | |
| 6,898,299 B1 | 5/2005 | Brooks | |
| 6,963,301 B2 | 11/2005 | Schantz | |
| 6,993,443 B2 | 1/2006 | Harle | |
| 7,096,148 B2 | 8/2006 | Anderson | |
| 7,298,314 B2 | 11/2007 | Schantz | |
| 7,307,595 B2 | 12/2007 | Schantz | |
| 7,373,271 B1 | 5/2008 | Schneider | |
| 7,394,254 B2 | 7/2008 | Rieke et al. | |
| 7,414,571 B2 | 8/2008 | Schantz | |
| 7,876,109 B2 | 1/2011 | Mohr | |
| 7,907,701 B2 | 3/2011 | Anderson | |
| 8,228,028 B2 | 7/2012 | Schneider | |
| 8,378,664 B2 | 2/2013 | Hinz | |
| 2003/0011359 A1 | 1/2003 | Ashe | |
| 2003/0078003 A1 | 4/2003 | Hunter | |
| 2003/0094940 A1 | 5/2003 | Duenisch | |
| 2003/0233042 A1 | 12/2003 | Ashe | |
| 2004/0030379 A1 | 2/2004 | Hamm | |
| 2004/0088136 A1 | 5/2004 | Ashe | |
| 2006/0122497 A1 | 6/2006 | Glossop | |
| 2006/0192550 A1 | 8/2006 | Sandquist | |
| 2006/0238199 A1 | 10/2006 | Larsen | |
| 2006/0273795 A1 | 12/2006 | Rieke et al. | |
| 2006/0293593 A1 | 12/2006 | Govari | |
| 2007/0078334 A1 | 4/2007 | Scully | |
| 2007/0270722 A1 | 11/2007 | Loeb | |
| 2007/0278008 A1 | 12/2007 | Kuckes | |
| 2008/0094057 A1 | 4/2008 | Ashe | |
| 2008/0162074 A1 | 7/2008 | Schneider | |
| 2009/0030646 A1 | 1/2009 | Jones | |
| 2009/0076746 A1 | 3/2009 | Higgins | |
| 2009/0105779 A1 | 4/2009 | Moore | |
| 2009/0195202 A1 | 8/2009 | Takeuchi | |
| 2009/0295391 A1 | 12/2009 | Bosnar | |
| 2010/0053789 A1 | 3/2010 | Duric | |
| 2010/0082280 A1 | 4/2010 | Schneider | |
| 2010/0250176 A1 | 9/2010 | Reene | |
| 2010/0315080 A1 | 12/2010 | Duncan | |
| 2012/0056616 A1 | 3/2012 | May | |
| 2012/0223699 A1 | 9/2012 | Holman | |
| 2012/0286786 A1 | 11/2012 | Schellekens et al. | |
| 2013/0166002 A1 | 6/2013 | Jung | |
| 2013/0296691 A1 | 11/2013 | Ashe | |
| 2014/0002063 A1* | 1/2014 | Ashe | A61B 8/4254 324/207.15 |
| 2014/0159707 A1 | 6/2014 | Ashe | |

\* cited by examiner

SYSTEM AND METHOD FOR MAGNETIC POSITION TRACKING

CLAIM OF PRIORITY

This application is a continuation application and claims priority under 35 USC §120 to U.S. patent application Ser. No. 13/534,666, filed Jun. 27, 2012, the entire contents of which are hereby incorporated by reference.

FIELD OF THE INVENTION

The present invention relates to an improved system and method for magnetic position tracking, and more particularly to a system and a method that reduces the magnetic field induced noise signal in the sensor interconnect system by periodically switching the polarity of the noise signal.

BACKGROUND OF THE INVENTION

Magnetic position tracking systems are becoming more widely used in the medical field, particularly when paired with an ultrasound imaging system. Due to the problems introduced into magnetic systems by conductive metals, medical magnetic tracking systems may operate in a low frequency band, in the sub 2 KHz range down to near DC levels. Distortion of the transmitted fields due to nearby conductive metals is minimized when operating in this low frequency range. A problem which arises due to these low frequencies is that the magnetic signals tend to be less affected by signal shielding materials such as aluminum or copper which are effective at higher frequencies. The shields for low frequency must employ high permeability materials and the design must be optimized such that leakage fields are well controlled. This makes the design of low frequency shielding much more difficult than for higher frequencies where thin conductive foils and loosely fitting shells can be employed. Due to the sensitive nature of the signals from the magnetic sensors, the signal path interconnect must be carefully designed to minimize sensitivity to the transmitted field. Electromotive force (EMF) errors are induced into the interconnect system if there is an unbalanced loop area within the interconnect system that is exposed to the transmitted field. In the case of an ultrasound probe, the probe interconnect system is designed to accommodate hundreds of co-axial cable elements and their associated terminations. This type of interconnect presents a relatively large unbalanced loop area into the signal path of the magnetic sensor.

Prior art systems have avoided this problem by running the optimized magnetic interconnect cable assembly adjacent to the probe interconnect cable assembly. The external mounting of the magnetic sensor and the bulk of a second independent cable running alongside the probe cable is objectionable to many end users. In order to disconnect a probe from the ultrasound chassis, both the probe interconnect and magnetic sensor interconnect must be disconnected. The mass of the probe interconnect, which is attached to the magnetic sensor cable and connector, stresses the smaller interconnect causing reliability concerns. Another limitation of prior art systems is seen when the sensor signals must be passed through a connector which shares the same physical structure as a therapeutic device, such as is found on an endoscope. In this case, the magnetic signal must be contained within the instrument due to size constraints. Currently, prior art systems employ magnetic shielding around the magnetic portion of the instrument connector. This shielding can become bulky, complex, and expensive. Sterilization and reprocessing are needed in order to safely re-use such an instrument, and these costs are moving the industry towards inexpensive disposable devices. The ability to pass the magnetic sensor signals through a single, uncomplicated, low cost interconnect, without adding large cost elements to the magnetic sensor, is thus very desirable.

SUMMARY OF THE INVENTION

In general, in one aspect, the invention features a system for magnetic position tracking of a device including a magnetic transmitter, a magnetic sensor, a computing system and a polarity inverter. The magnetic transmitter includes at least one transmitter coil that outputs a transmitted magnetic field having a time derivative component. The magnetic sensor includes at least one sensor coil that has coil terminals having a polarity, and the sensor coil is responsive to the time derivative component of the transmitted magnetic field and outputs a sensor signal. The computing system computes position and angular orientation data of a device based on the sensor signal and the polarity inverter is configured to connect to the coil terminals and to cause the polarity of the coil terminals to be reversed according to a switching signal.

Implementations of this aspect of the invention may include one or more of the following features. The system may further include a sign inverter configured to invert a digitized output from an analog to digital (A/D) converter. The sign inverter is operated concurrently with the switching signal, so that the polarity of the coil terminals is maintained at the computing system's input. The system may further include a synchronizer configured to operate concurrently with the magnetic transmitter. The system may further include averaging means. The sign inverter is also configured to invert the sensor signal at the A/D converter's input. The transmitted magnetic field may be a sinusoid. The sinusoid may include a plurality of sine waves. The sinusoid may be continuous with respect to time. The sinusoid may be time division multiplexed. The transmitted magnetic field may have one of trapezoidal, triangular, half sinusoid, exponential, or square amplitude versus time characteristics shape. The polarity inverter is located adjacent to the magnetic sensor. The polarity inverter is connected to the magnetic sensor via a twisted pair cable. The polarity inverter may be an analog switch. The switching signal is transmitted wirelessly or via a wired connection. The averaging means is configured to sum signals received with opposite polarity from the sign inverter. The averaging means may be a lowpass filter.

In general, in another aspect, the invention features a method for magnetic position tracking of a device including the following steps. Providing a magnetic transmitter having at least one transmitter coil. The transmitter coil outputs a transmitted magnetic field having a time derivative component. Providing a magnetic sensor having at least one sensor coil. The sensor coil has coil terminals having a polarity, and the sensor coil is responsive to the time derivative component of the transmitted magnetic field and outputs a sensor signal. Providing a computing system for computing position and angular orientation data of a device based on the sensor signal and providing a polarity inverter configured to connect to the coil terminals and to cause the polarity of the coil terminals to be reversed according to a switching signal.

This invention is applicable to electromagnetic tracking of medical instruments. Applications include tracking of instruments such as ultrasound probes, biopsy needles, ablation instruments, and so on.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views.

DETAILED DESCRIPTION OF THE INVENTION

The ideal magnetic tracking system receives 100% of its signal input exclusively from the sensor coil, where the sensor signal is a response to a transmitted time varying magnetic field. The sensor coil signal traverses the sensor assembly interconnect system travelling from the sensor coil through cable wires, to and through the connector, and through signal conditioning such as an amplifier and analog-to-digital converter mounted on a printed circuit board. The interconnect system components generate spurious signals in response to the transmitted time varying magnetic field. These spurious signals sum to corrupt the otherwise ideal sensor coil signal, and thus induce position and orientation error of the tracked instrument.

The invention described herein electronically periodically switches polarity of the summed spurious signal, enabling its self-cancellation. The invented polarity switch method and apparatus is applied to remove the spurious error-inducing signals generated within the interconnect, leaving the desired sensor coil signal uncorrupted.

Figure 1:
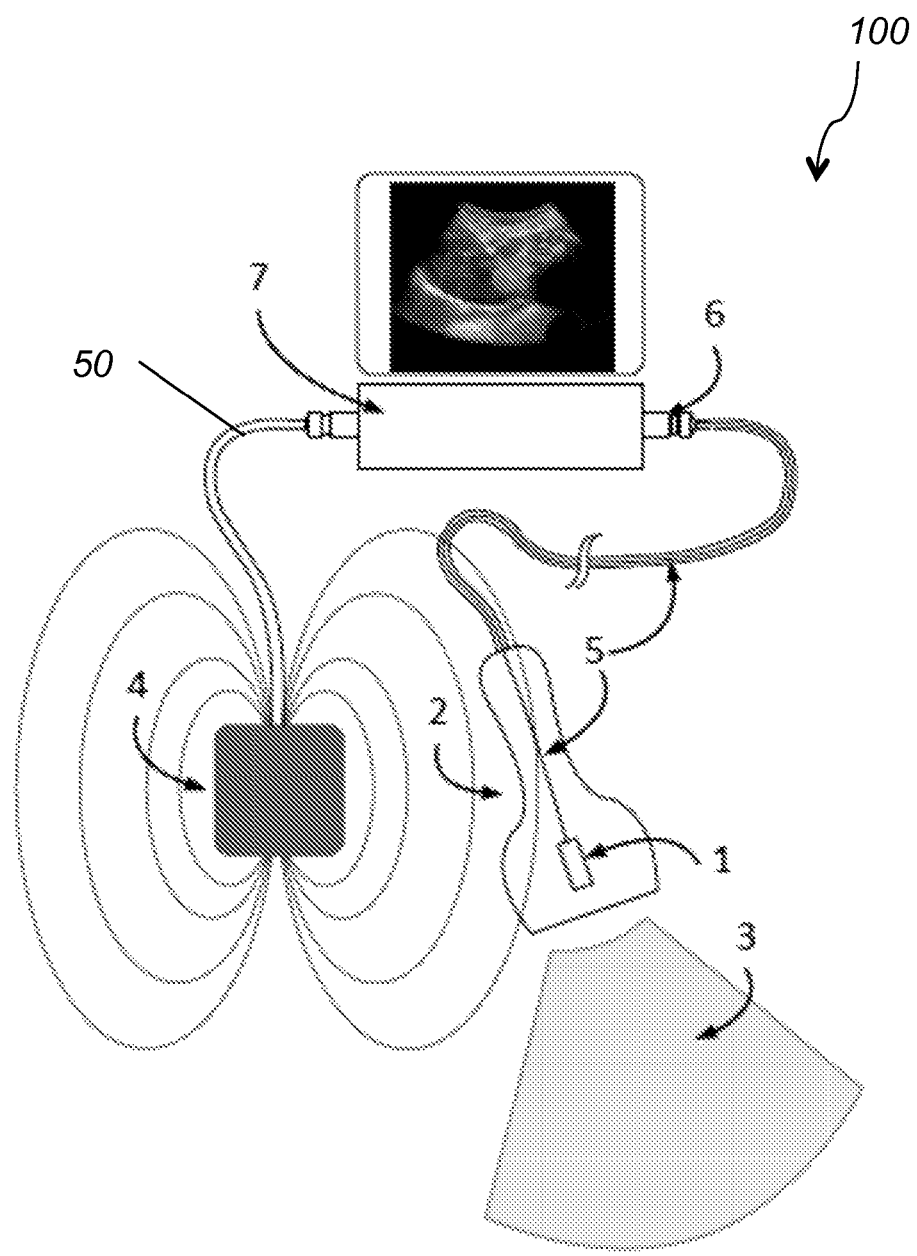
FIG. 1 illustrates a schematic of a magnetic transmitter and sensor integrated with an ultrasound imaging system.

Referring to FIG. 1, a magnetic position tracking system 100 includes a magnetic sensor 1, a magnetic transmitter 4, a computer 7 and an instrument 2 whose position is being tracked. Magnetic sensor 1 is connected to the computer 7 via cable 5 and connector 6. Magnetic transmitter 4 is connected to computer 7 via cable 50. Magnetic sensor 1 outputs signals in response to the time derivative of magnetic fields, $$\frac{dB}{dt},$$

generated by the magnetic transmitter 4. Computer 7 receives the output signals from the magnetic sensor 1 by way of cable 5 and connector 6 and computes the position of magnetic sensor 1 relative to the magnetic transmitter 4.

Magnetic sensor 1 may contain one or more signal channels. In one example, a typical 6 degree of freedom magnetic position tracking system may be constructed using 3 signal channels within magnetic sensor 1 combined with 3 orthogonal magnetic transmitting coils housed within transmitter 4. For better clarity in this description, a single signal channel is described, because the operation of any additional signal channel is identical.

Figure 2:
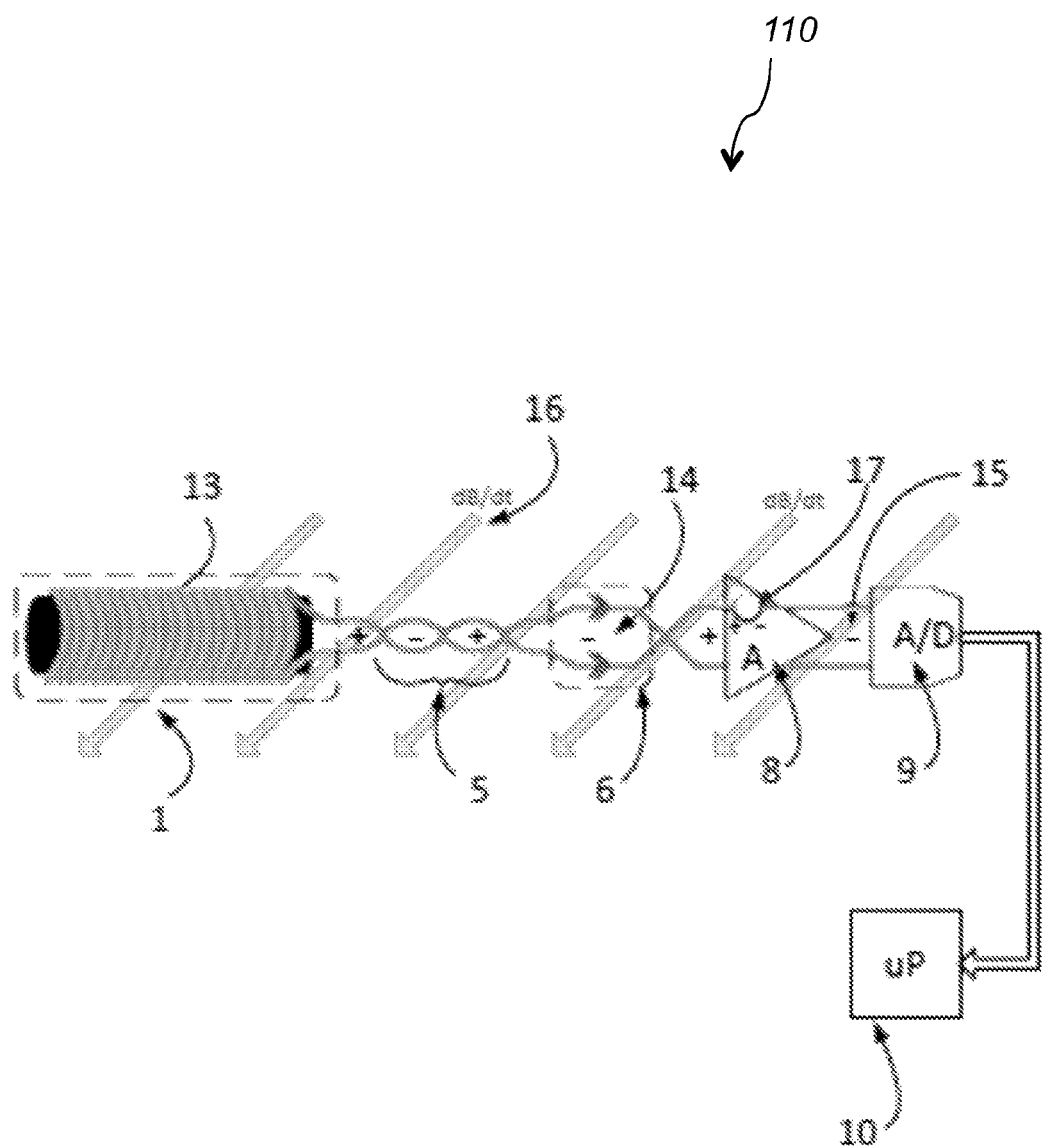
FIG. 2 illustrates a schematic of prior art magnetic sensor cable and signal conditioning elements.

Referring to FIG. 2, a single signal channel magnetic position tracking system 110, includes a magnetic sensor coil 13, a connector 6, an amplifier 8, an analog to digital (A/D) converter 9 and a processor 10. Coil 13 is connected to the amplifier 8 via a pair of twisted wires 5 and via connector 6. The sensing signal passes through the amplifier 8, then through the A/D converter 9 and then goes to processor 10.

Coil 13 detects the time derivative of the magnetic field, dB/dt, generated by the transmitter 4 according to the formula $$EMF_{coil} = A * N * U * \frac{dB}{dt}$$

A=area of coil 13 in square meters
N=number of turns in coil 13
U=free space permeability
dB/dt=time rate of change of the magnetic flux density, B, from transmitter 4, in Tesla per second.

It is important to ensure that coil 13 is the only element of magnetic sensor 1 that is responsive to the magnetic signal from transmitter 4. Any additional signal sources between coil 13 and A/D converter 9 will result in an incorrect position computation for sensor 1. Prior art systems depend upon a high quality twisted pair cable 5 to conduct the EMF from coil 13 to connector 6. The twisted pair cable 5 provides cancellation of magnetic signals by way of forming small opposing loops along its length, causing the EMF of each successive loop to change polarity with respect to its neighbors and thereby to cancel the effects of any external magnetic fields. This cancellation works well in a uniform magnetic field. However, in a gradient magnetic field, the dB/dt magnitude is not uniform along cable 5 and therefore the EMF for successive loops is not uniform. In this case cable 5 introduces a cable error, $EMF_{cable}$. $EMF_{cable}$ has the highest magnitude when cable 5 is placed on or near the transmitter 4, due to the high gradient field near the transmitter 4. An example of this occurrence is when instrument 2 is an ultrasound transducer and the operator inadvertently pulls cable 5 across the transmitter 4.

An additional source of error occurs where the signals from coil 13 pass through connector 6. In most high density pin type connectors, the pins form a parallel path over their mating length. This path has a net area described by the product of pin length and pin separation. This net area is shown as a connector pin loop 14 in FIG. 2. The EMF from connector pin loop 14 is then described as:

$$EMF_{connector} = L_{pin} * W_{pin} * U * \frac{dB}{dt}$$

$L_{pin}$=length of a connector pin
$W_{pin}$=pin separation distance
U=free space permeability dB/dt=time rate of change of the magnetic flux density, B, from transmitter 4

An important factor with the EMF error from loop 14 is that loop 14 may be located near transmitter 4 while sensor 1 may be near the outside limits of its range. Thus dB/dt at loop 14 may be orders of magnitude larger than the dB/dt at coil 13. This could occur, for example, if an ultrasound operator positions computer 7 and connector 6 near the transmitter 4 due to space constraints in a procedure room. Prior art systems commonly place a restriction on the position of the connector 6 relative to the transmitter 4, a common restriction being 0.6 meters of minimum separation. Prior art systems also commonly employ a magnetic shield around connector 6, to decrease the dB/dt magnitude at loop 14. Such a shield adds cost and bulk to connector 6, and can cause distortion of the magnetic field transmitted by transmitter 4 if placed too closely.

An additional source of EMF error is the net loop area of the printed circuit board traces, as the physical paths of the signal lines through amplifier 8 and into A/D 9 are separate. The loop formed by these printed circuit board traces is shown by trace area 15 in FIG. 2. Trace area 15 error is important because circuitry used to energize transmitter 4 is contained within computer 7 and there is commonly some leakage dB/dt from this circuitry. Since it is desirable to fit computer 7 into a small form factor, the spacing between this energizing circuitry and trace area 15 may be only a few tens of millimeters. This can result in a significant leakage dB/dt component being present at trace area 15, giving:

$$EMF_{trace} = A_{trace} * U * \frac{dB}{dt}$$

$A_{trace}$=trace loop area
U=free space permeability
dB/dt=time rate of change of the magnetic flux density, B, from transmitter 4

Prior art systems protect area 15 using magnetic shielding and also attempt to locate the transmitter drive circuitry as far from area 15 as is practical.

Once the signal from coil 13 is digitized by the A/D converter 9 it is no longer susceptible to dB/dt effects from transmitter 4 and is processed by processor 10.

The total signal at the input of the A/D converter 9 is thus;

$EMF_{total}$=$EMF_{coil}$+$EMF_{cable}$+$EMF_{connector}$+$EMF_{trace}$

The last three terms of this equation are significant errors that need to be minimized.

Figure 3:
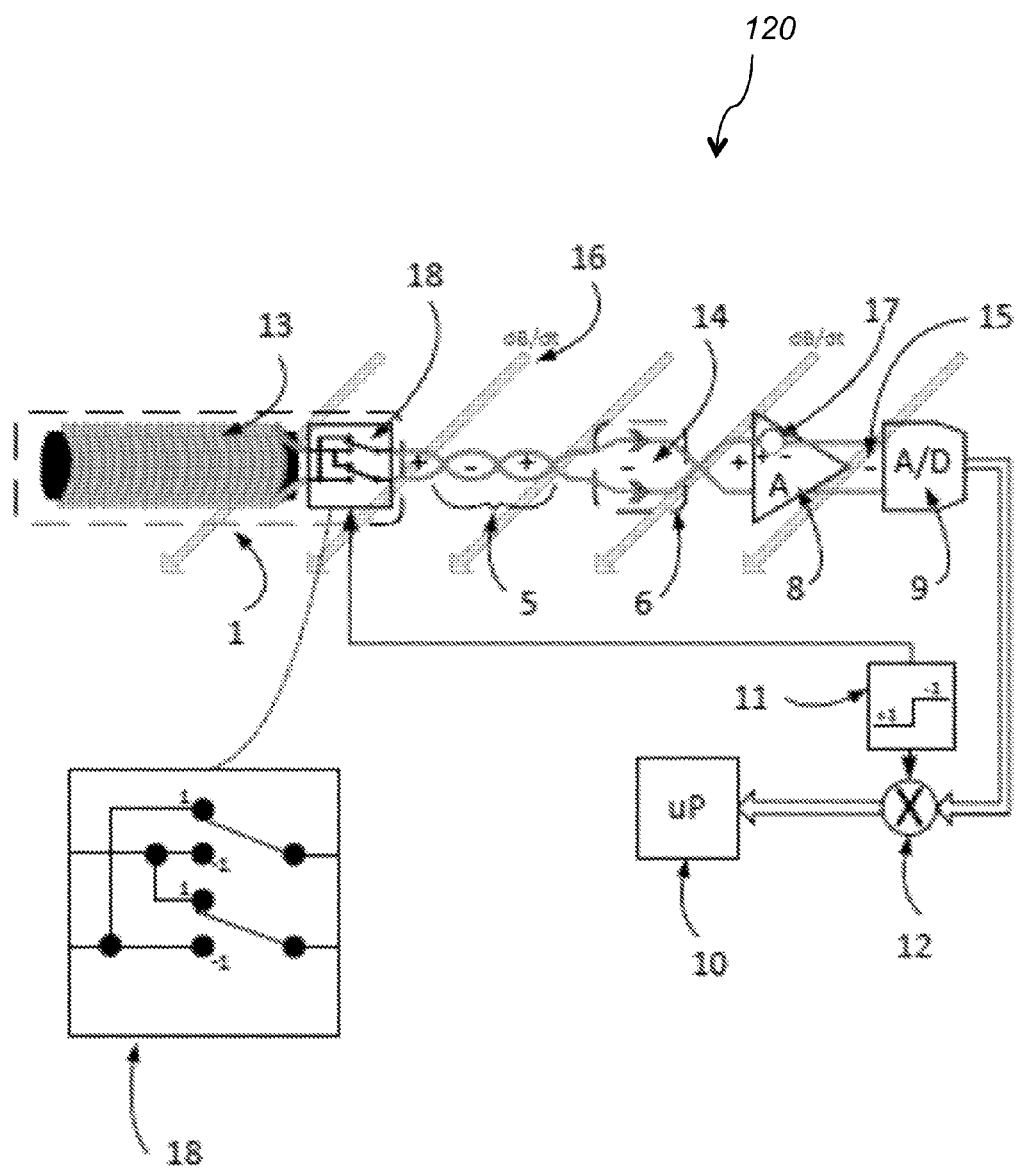
FIG. 3 illustrates a schematic of the magnetic sensor cable with improved signal conditioning elements.

The above mentioned cable, connector and trace errors ($EMF_{coil}$, $EMF_{connector}$, $EMF_{trace}$) are minimized in the present invention by periodically switching the polarity of the noise signal. Referring to FIG. 3, in one embodiment of the present invention, a single signal channel magnetic position tracking system 120, includes a magnetic sensor coil 13, a connector 6, a dual single-pole-double-throw (SPDT) analog switch 18, an amplifier 8, an analog to digital (A/D) converter 9, a polarity control 11, a multiplier 12 and a processor 10. Coil 13 is connected to the amplifier 8 via a pair of twisted wires 5 and via connector 6. The sensing signal passes through the SPDT analog switch 18, the amplifier 8, then through the A/D converter 9, then through the multiplier 12 and then goes to processor 10. Multiplier 12 also receives information from the polarity control 11. Polarity control 11 controls the polarity of the sensor signal at the end of the coil terminals. Polarity control 11 is set to output a logic 0 or a logic 1. Logic 0 is interpreted by multiplier 12 and switch 14 as normal or non-inverting polarity (value=1) and logic 1 is interpreted as inverted polarity (value=−1). The effect of switch 18 and multiplier 12 is to negate the polarity of coil 13 as seen by the A/D converter 9, and to simultaneously negate the data from the A/D converter 9 as seen by processor 10. The net effect is that the signal from coil 13 as seen by processor 10 does not change sign regardless of the state of polarity control 11. The error inputs, $EMF_{cable}$, $EMF_{connector}$, and $EMF_{trace}$, however, change polarity at processor 10 in accordance with the state of polarity control 11.

Figure 4:
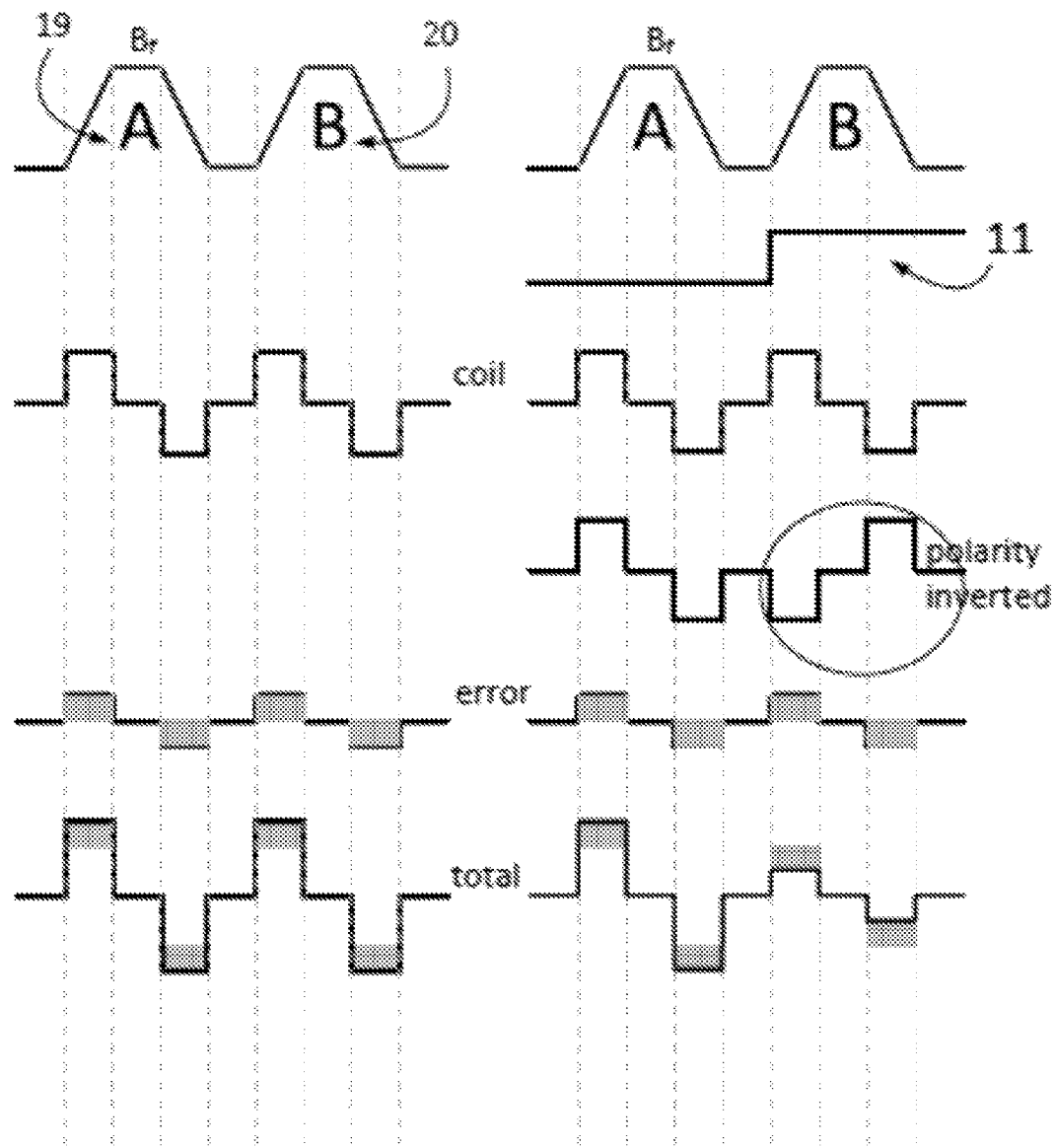
FIG. 4 illustrates states and transitions of a single-channel DC pulsed magnetic sensor signal with and without the improved signal conditioning elements.

Referring to FIG. 4, the state of polarity control 11 is synchronized with the operation of transmitter 4 so that it is logic 0 (non-inverting) during the first pulse A 19 and logic 1 (inverting) during the second pulse B 20. $EMF_{total}$ for the rising and falling edges of pulse 19 are integrated within processor 10 to produce an output proportional to $EMF_{coil}$+$EMF_{cable}$+$EMF_{connector}$+$EMF_{trace}$ This equation is described in U.S. Pat. No. 6,172,499, the contents of which are expressly incorporated herein by reference. At the boundary between pulse 19 and pulse 20, polarity control 11 is switched to logic 1 and multiplier 12 is set to negate data from A/D 9. The $EMF_{total}$ for the rising and falling edges of pulse B is integrated within processor 10 to produce an output proportional to $EMF_{coil}$−$EMF_{cable}$−$EMF_{connector}$−$EMF_{trace}$ If we add the integral results from first pulse 19 and second pulse 20 and divide by two, the resulting average is an integral proportional only to $EMF_{coil}$. Since the positions of computer 7, connector 6, and portions of cable 5 are relatively stable with respect to transmitter 4, the magnitudes of $EMF_{cable}$, $EMF_{connector}$, and $EMF_{trace}$ remain essentially constant during the pulse AB sequence. The present invention thus eliminates the need to shield loop 14, area 15, and eliminates gradient error from cable 5.

Placing a lowpass filter at the output of multiplier 12 can also accomplish the averaging function of the first pulse 19 and second pulse 20 sequence. The lowpass filter should be chosen such that the ripple at the output of multiplier 12 as an amplitude function of $EMF_{cable}$+$EMF_{connector}$+$EMF_{trace}$ is within acceptable limits and the system response bandwidth is adequately fast. For example, in a system employing the present invention, a 4th order infinite impulse response (IIR) filter, implemented in a digital signal processor (DSP), with a cutoff frequency of 2 Hz is adequate for a system employing a three axis transmitter 4 and a three axis sensor 1 operating at 240 transmitter pulses per second.

In addition to magnetic EMF error cancellation, the present invention may also be employed to remove EMF errors from sources such as ground coupling. Current from computer 7 flowing into transmitter 4 may induce some resistive voltage drops within the conductors of computer 7. One important conductor is the grounding system. Generally the circuitry will employ a ground plane on a printed circuit board. This ground plane generally has a small but measurable resistance, on the order of a milliohm for points a few centimeters apart. Imperfections in amplifier 8, ground feedthrough from biasing circuitry, and numerous other parasitic sources can cause error signals to appear at the output of amplifier 8. Collectively these EMF error sources are shown as circuit error source 17. Source 17 will exhibit a reasonably constant response to each of pulse 19 and pulse 20 in FIG. 4. Due to the constant nature of this response, the multiplier 12 and polarity control 11 will cause the error from source 17 to be periodically inverted. The error source 17 is thus removable by averaging or lowpass filtering as previously described.

Figure 5:
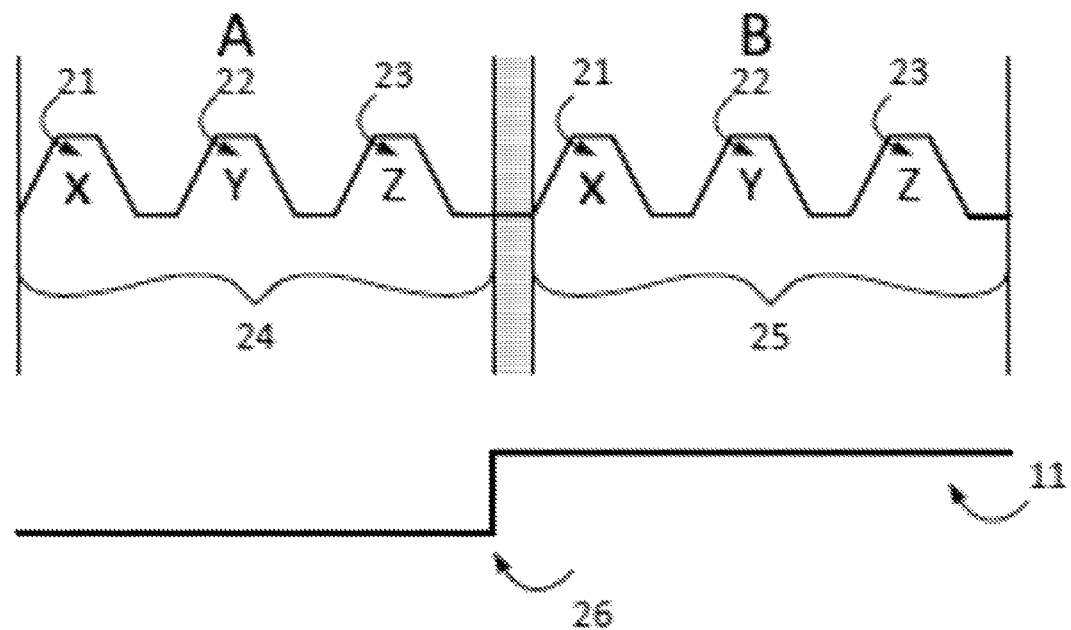
FIG. 5 illustrates extension of the single-channel DC pulsed magnetic sensor signal to a three channel magnetic sensor signal stream with polarity switch timing.

Referring to FIG. 5, in another embodiment of the present invention, pulse 19 and pulse 20 are each comprised of multiple pulses. In this example, transmitter 4 is comprised of 3 orthogonal coils, referred to as X,Y, and Z respectively, energized sequentially. X axis pulse 21 represents the X coil excitation, Y axis pulse 22 represents the Y coil excitation, and Z axis pulse 23 represents the Z coil excitation. The combination of pulses 21, 22, and 23 herein referred to first transmitter sequence 24 and second transmitter sequence 25. Using the device described in U.S. Pat. No. 6,172,499, as an example, the response of sensor 1 to each of the pulses 21, 22, 23 in first sequence 24 is processed in the same manner as previously disclosed for first pulse 19 and stored. Next, polarity control 11 is switched and the response of sensor 1 to each of the pulses 21, 22, 23 in second sequence 25 is computed and averaged with the corresponding response values from first sequence 24. The sequence of FIG. 5 is useful because analog switch 18 may have some undesirable parasitic error effects on the output of coil 13. One such effect is commonly known as charge injection. The injection components change amplitude and polarity synchronously with polarity control 11 and thus appear as a transient offset at the output of multiplier 12. Introducing a short amount of dead time 26 between the first sequence 24 and the second sequence 25 will allow this transient offset to decay to zero before being sampled by processor 10.

Figure 6:
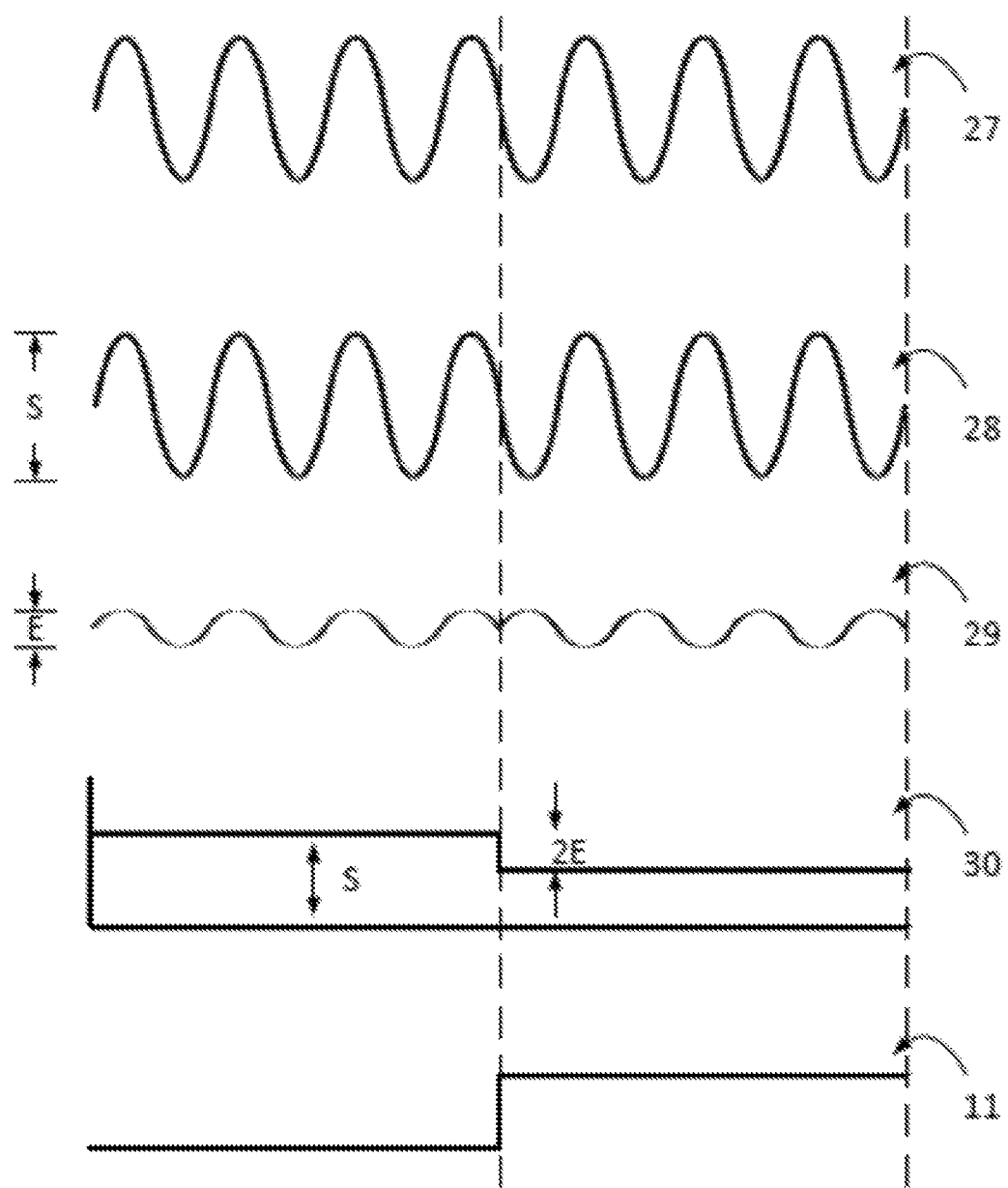
FIG. 6 illustrates application of the improved signal conditioning schema to a single-channel AC driven magnetic sensor signal with polarity switch timing.

The system of FIG. 3, may also be use for error reduction in an AC magnetic tracking system. FIG. 6 shows a pictorial description of key waveforms present at the input of processor 10 when the system 120 of FIG. 3 is operated to cancel transmitter induced offset signals in an AC magnetic tracking system. Transmitter 4 emits an AC magnetic field 27. Sensor coil 13 outputs an EMF proportional to the time derivative of magnetic field 27 according to the formula $$EMF_{coil} = A*N*U*B*\sin \omega t$$

A=area of coil 13 in square meters
N=number of turns in coil 13
U=free space permeability
B=peak to peak magnitude of field, in Tesla
$\omega$=angular frequency of magnetic field, in radians per second
t=time, in seconds Parasitic, unbalanced loops exposed to the magnetic field from transmitter 4 are added to the signal from coil 13 and the digitized signal at processor 10 is described as $$EMF_{total} = (EMF_{coil} + EMF_{cable} + EMF_{connector} + EMF_{trace})*\sin \omega t$$

$EMF_{coil} \sin \omega t$ = signal from coil 13 due to magnetic field from transmitter 4
$EMF_{cable} \sin \omega t$ = induced EMF due to gradient field of transmitter 4 acting on cable 5.
$EMF_{connector} \sin \omega t$ = induced EMF in connector pin loop 14 due to magnetic field from transmitter 4.
$EMF_{trace} \sin \omega t$ = induced EMF from printed circuit board trace loops
$EMF_{trace} \sin \omega t$ = induced EMF in trace area 15 due to magnetic field from transmitter 4

Ideally, $EMF_{coil} \sin \omega t$ would be the only signal digitized by the A/D converter 9 and processed by processor 10 and by a demodulator. $EMF_{cable} \sin \omega t$, $EMF_{connector} \sin \omega t$, and $EMF_{trace} \sin \omega t$ are undesireable signals.

The total signal at the A/D converter 9 due to transmitter 4 is described as $$EMF_{total} = (EMF_{coil} + EMF_{cable} + EMF_{connector} + EMF_{trace})*\sin \omega t$$

After demodulation and detection in processor 10, the value corresponding to $EMF_{total}$ is stored and the polarity control 11 is switched. The output of the A/D converter 9 is then equal $$EMF_{total} = (EMF_{coil} - EMF_{cable} - EMF_{connector} - EMF_{trace})*\sin \omega t$$

Demodulating and detecting this second sequence and averaging with the stored result from the first results in an output value proportional only to $EMF_{coil}$. It should be noted that it is not required that the AC magnetic field 27 be continuous, nor fixed in frequency. The technique shown will work with time division multiplexed AC magnetic fields, and with fixed, variable, or multiple frequencies.

In the embodiment of FIG. 6, the gain of amplifier 8 was set to unity to simplify the expressions. The waveforms are shown in continuous time format for clarity purposes, although in actuality the waveforms shown in FIG. 6 are discrete digital values output by the A/D converter 9. FIG. 6, assumes that the sampling rate of the A/D converter 9 is high enough to accurately capture the details shown.

The embodiment of FIG. 3 may be employed on numerous other signal transmission methods used in magnetic tracker art by employing the following principals:

1) Define a measurement sequence, including magnetic transmitter excitations and receipt of magnetic signals from sensor coils.

2) Feeding coil signals into a switching array capable of reversing the coil polarity relative to subsequent interconnect and processing elements. The switching array should be located such that parasitic loops are located between the switching array and the A/D converter.

3) Controlling the switching array such that the processor receiving A/D data inverts the data synchronously with coil polarity changes at the output of the switching array.

4) Alternating the polarity of the switching array and A/D sign inversion such that these operations are synchronous with the defined magnetic transmitter excitation sequences.

5) Averaging alternate sign inverted processed data sequences such that the offset components cancel, or alternatively low pass filtering the processed data sequence, or alternatively storing a sequence of a first polarity, subtracting a sequence of opposing polarity, and utilizing the remainder offset value to correct future readings.

Several embodiments of the present invention have been described. Nevertheless, it will be understood that various modifications may be made without departing from the spirit and scope of the invention. Accordingly, other embodiments are within the scope of the following claims.

What is claimed is:

1. A system for magnetic position tracking of a device comprising:
 a transmitter configured to transmit a magnetic field having a time derivative component;
 a sensor including terminals having a polarity, wherein the sensor is responsive to the time derivative component of the transmitted magnetic field and outputs a sensor signal;
 a computing system for computing data representative of one or both of position and angular orientation of a device based on the sensor signal; and a polarity inverter configured to cause the polarity of the terminals to be reversed according to a switching signal, wherein magnetic field errors that are caused by conductors that are responsive to the time derivative component of the transmitted magnetic field are substantially removed from the sensor signal.

2. The system of claim 1, wherein the conductors comprise conductive connections.

3. The system of claim 1, wherein the conductors comprise one or both of a connector and a trace.

4. The system of claim 1, wherein the transmitter comprises a magnetic transmitter including at least one coil.

5. The system of claim 1, wherein the sensor comprises a magnetic sensor including at least one coil.

6. The system of claim 1, wherein the polarity inverter is configured to connect to the terminals.

7. The system of claim 1, further comprising a sign inverter configured to invert a digitized output from an analog to digital (A/D) converter, wherein the sign inverter is operated concurrently with the switching signal such that the polarity of the terminals is maintained at an input of the computing system.

8. The system of claim 7, further comprising a synchronizer configured to operate concurrently with the transmitter.

9. The system of claim 7, wherein the sign inverter is configured to invert the sensor signal at an input of the A/D converter.

10. The system of claim 1, wherein the transmitted magnetic field represents a time division multiplexed signal.

11. The system of claim 1, the transmitted magnetic field being representable by one or more of a trapezoidal, a triangular, a half sinusoid, an exponential, and a square amplitude versus time characteristics shape.

12. The system of claim 1, wherein the polarity inverter is located adjacent to the sensor.

13. The system of claim 1, wherein the polarity inverter is configured to connect to the sensor via a twisted pair cable.

14. The system of claim 1, wherein the polarity inverter comprises an analog switch.

15. The system of claim 1, wherein the switching signal is transmitted wirelessly.

16. The system of claim 7, further comprising averaging means configured to sum signals received with opposite polarity from the sign inverter.

17. The system of claim 16, wherein the averaging means comprises a lowpass filter.

18. A method for magnetic position tracking of a device comprising:

providing a transmitter configured to transmit a magnetic field having a time derivative component;

providing a sensor including terminals having a polarity, wherein the sensor is responsive to the time derivative component of the transmitted magnetic field and outputs a sensor signal;

providing a computing system for computing data representative of one or both of position and angular orientation of a device based on the sensor signal;

providing a polarity inverter configured to cause the polarity of the terminals to be reversed according to a switching signal; and substantially removing, from the sensor signal, magnetic field errors that are caused by conductors that are responsive to the time derivative component of the transmitted magnetic field.

19. The method of claim 18, wherein the conductors comprise conductive connections.

20. The method of claim 18, wherein the conductors comprise one or both of a connector and a trace.

21. The method of claim 18, wherein the transmitter comprises a magnetic transmitter including at least one coil.

22. The method of claim 18, wherein the sensor comprises a magnetic sensor including at least one coil.

23. The method of claim 18, wherein the polarity inverter is configured to connect to the terminals.

24. A method comprising:

transmitting, by a transmitter, a magnetic field having a time derivative component;

outputting, by a sensor that is responsive to the time derivative component of the transmitted magnetic field, a sensor signal;

computing data representative of one or both of position and angular orientation of the sensor based on the sensor signal;

reversing a polarity of terminals of the sensor according to a switching signal; and substantially removing, from the sensor signal, magnetic field effects that are caused by conductors that are responsive to the time derivative component of the transmitted magnetic field.

25. The method of claim 24, wherein the conductors comprise conductive connections.

26. The method of claim 24, wherein the conductors comprise one or both of a connector and a trace.

27. The method of claim 24, wherein the transmitter comprises at least one transmitter coil.

28. The method of claim 24, wherein the sensor comprises at least one sensor coil.

* * * * *